United States Patent
Böss et al.

(10) Patent No.: US 8,455,502 B2
(45) Date of Patent: *Jun. 4, 2013

(54) SELECTIVE PHOSPHODIESTERASE 9A INHIBITORS AS MEDICAMENTS FOR IMPROVING COGNITIVE PROCESSES

(75) Inventors: Frank-Gerhard Böss, Wuppertal (DE); Christina Erb, Kriftel (DE); Martin Hendrix, Odenthal (DE); Marja Van Kampen, Neu-Isenburg (DE); Frank Wunder, Wuppertal (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

This patent is subject to a terminal disclaimer.

(21) Appl. No.: 12/769,166

(22) Filed: Apr. 28, 2010

(65) Prior Publication Data

US 2010/0210839 A1   Aug. 19, 2010

Related U.S. Application Data

(63) Continuation of application No. 10/525,119, filed as application No. PCT/EP03/08880 on Aug. 11, 2003, now Pat. No. 7,737,156.

(30) Foreign Application Priority Data

Aug. 23, 2002 (DE) .................................. 10238722

(51) Int. Cl.
  *A61K 31/59*   (2006.01)
  *A61K 31/415*   (2006.01)

(52) U.S. Cl.
  USPC ........................................ 514/262.1; 514/406

(58) Field of Classification Search
  USPC .............................................. 514/262.1, 406
  See application file for complete search history.

(56) References Cited

U.S. PATENT DOCUMENTS

| | | |
|---|---|---|
| 3,165,520 A | 1/1965 | Schmidt et al. |
| 3,169,965 A | 2/1965 | Schmidt et al. |
| 3,211,731 A | 10/1965 | Schmidt et al. |
| 3,732,225 A | 5/1973 | Breuer et al. |
| 5,002,949 A | 3/1991 | Peseckis et al. |
| 5,041,449 A | 8/1991 | Belleau et al. |
| 5,047,407 A | 9/1991 | Belleau et al. |
| 5,053,499 A | 10/1991 | Kojima et al. |
| 5,256,668 A | 10/1993 | Hsu et al. |
| 5,270,315 A | 12/1993 | Belleau et al. |
| 5,294,612 A | 3/1994 | Bacon et al. |
| 5,466,806 A | 11/1995 | Belleau et al. |
| 5,541,187 A | 7/1996 | Bacon et al. |
| 5,563,049 A | 10/1996 | Kojima et al. |
| 5,656,629 A | 8/1997 | Bacon et al. |
| 5,684,164 A | 11/1997 | Belleau et al. |
| 5,750,673 A | 5/1998 | Martin |
| 5,969,116 A | 10/1999 | Martin |
| 5,977,118 A | 11/1999 | Bacon et al. |
| 5,977,332 A | 11/1999 | Martin |
| 6,100,037 A | 8/2000 | Phillips et al. |
| 6,174,884 B1 | 1/2001 | Haning et al. |
| 6,175,008 B1 | 1/2001 | Belleau et al. |
| 6,211,158 B1 | 4/2001 | Seela et al. |
| 6,225,315 B1 | 5/2001 | Ellis |
| 6,350,753 B1 | 2/2002 | Belleau et al. |
| 6,458,796 B1 | 10/2002 | Haning et al. |
| 6,831,174 B2 | 12/2004 | Belleau et al. |
| 6,903,224 B2 | 6/2005 | Belleau et al. |
| 7,067,507 B2 | 6/2006 | Pulley et al. |
| 7,122,693 B2 | 10/2006 | Belleau et al. |
| 7,351,827 B2 | 4/2008 | Howell et al. |
| 7,488,733 B2 | 2/2009 | Hendrix et al. |
| 7,615,558 B2 | 11/2009 | Hendrix et al. |
| 7,737,156 B2 | 6/2010 | Böβ et al. |
| 2001/0041797 A1 | 11/2001 | Belleau et al. |
| 2001/0044441 A1 | 11/2001 | Campbell et al. |
| 2002/0058635 A1 | 5/2002 | Averett |
| 2002/0132754 A1 | 9/2002 | Boss et al. |
| 2003/0087918 A1 | 5/2003 | Belleau et al. |
| 2004/0220186 A1 | 11/2004 | Bell et al. |
| 2004/0254201 A1 | 12/2004 | Belleau et al. |
| 2004/0266736 A1 | 12/2004 | Wunder et al. |
| 2005/0209251 A1 | 9/2005 | Linker et al. |
| 2006/0100222 A1 | 5/2006 | Boss et al. |
| 2006/0106035 A1 | 5/2006 | Hendrix et al. |
| 2006/0111372 A1 | 5/2006 | Hendrix et al. |

(Continued)

FOREIGN PATENT DOCUMENTS

| | | |
|---|---|---|
| CA | 1 311 201 | 12/1992 |
| CA | 2 283 211 A1 | 9/1998 |

(Continued)

OTHER PUBLICATIONS

Bernabeu R, Schmitz P, Faillace MP, lzquierdo I, Medina JH. Hippocampal cGMP and cAMP are differentially involved in memory processing of inhibitory avoidance learning. Neuroreport. Jan 31, 1996;7(2):585-8 (abstract only provided).*

Farlow MR. Pharmacokinetic profiles of current therapies for Alzheimer's disease: implications for switching to galantamine. Clin Ther. 2001;23 Suppl A:A13-24.*

Intelihealth, "Alzheimer's disease," online, accessed Jun. 30, 2008, http://www.intelihealth.com/IH/intlh/WSIHWO00/8303/9117/195703.html?d=dmtHealthAZ.*

Intelihealth, "Dementia," online, accessed Sep. 22, 2009, http://www.intelihealth.com/IH/ihtIH/WSIHW000/24479/11184.html.*

Intelihealth, "Parkinson's disease," online, accessed Sep. 22, 2009, http://www.intelihealth.com/IH/ihtIH?d=dmtHealthAZ&c=201957.*

(Continued)

*Primary Examiner* — Paul Zarek

(74) *Attorney, Agent, or Firm* — Michael P. Morris; Edouard G. Lebel; Edward S. Lazer

(57) ABSTRACT

The invention relates to the use of selective phosphodiesterase 9A (PDE9A) inhibitors for producing medicaments for improving perception, concentration, cognitive processes, learning and/or memory.

9 Claims, 3 Drawing Sheets

U.S. PATENT DOCUMENTS

Figure 1:
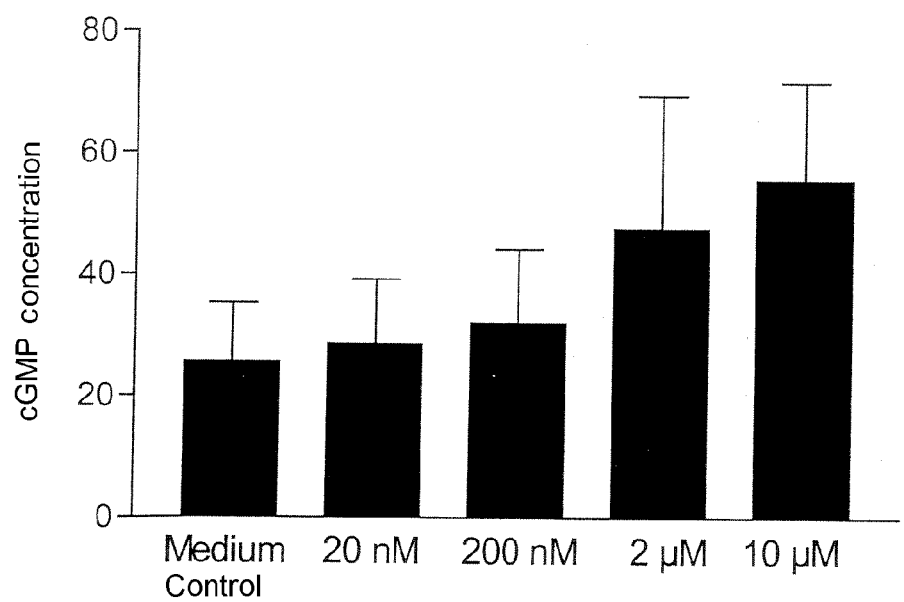

| | | | |
|---|---|---|---|
| 2006/0258651 A1 | 11/2006 | Linschoten et al. |
| 2007/0037977 A1 | 2/2007 | Belleau et al. |
| 2007/0105876 A1 | 5/2007 | Hendrix et al. |
| 2007/0105881 A1 | 5/2007 | Hendrix et al. |
| 2007/0161662 A1 | 7/2007 | Hendrix et al. |
| 2008/0255118 A1 | 10/2008 | Hendrix et al. |
| 2009/0111838 A1 | 4/2009 | Hendrix et al. |
| 2010/0035900 A1 | 2/2010 | Hendrix et al. |
| 2010/0210839 A1 | 8/2010 | Boess et al. |
| 2011/0015193 A1 | 1/2011 | Eickmeier et al. |
| 2011/0065730 A1 | 3/2011 | Hendrix et al. |
| 2011/0082137 A1 | 4/2011 | Giovannini et al. |

FOREIGN PATENT DOCUMENTS

| | | |
|---|---|---|
| CA | 2 438 890 A1 | 9/2002 |
| CA | 2 417 631 A1 | 1/2003 |
| CA | 2 466 824 | 5/2003 |
| CA | 2 484 997 A1 | 11/2003 |
| CA | 2 496 194 A1 | 3/2004 |
| CA | 2 496 292 A1 | 4/2004 |
| CA | 2 496 308 A1 | 4/2004 |
| CA | 2 524 900 | 11/2004 |
| CH | 396 923 | 8/1965 |
| CH | 396 924 | 8/1965 |
| CH | 396 925 | 8/1965 |
| CH | 396 926 | 8/1965 |
| CH | 396 927 | 8/1965 |
| CH | 398 626 | 3/1966 |
| DE | 1 147 234 | 4/1963 |
| DE | 1 149 013 | 5/1963 |
| DE | 1 153 023 | 8/1963 |
| DE | 1 156 415 | 10/1963 |
| DE | 2 408 096 | 2/1974 |
| DE | 4 004 558 | 9/1990 |
| DE | 101 56 249 A1 | 5/2003 |
| DE | 102 38 722 | 3/2004 |
| EP | 0 130 735 A1 | 1/1985 |
| EP | 0 286 028 | 10/1988 |
| EP | 496 617 | 7/1992 |
| EP | 0 626 387 | 11/1994 |
| EP | 0 679 657 | 11/1995 |
| EP | 0 995 751 A2 | 4/2000 |
| EP | 1 460 077 | 9/2004 |
| GB | 937 723 | 9/1963 |
| GB | 937 724 | 9/1963 |
| GB | 937 726 | 9/1963 |
| GB | 973 361 | 10/1964 |
| JP | 11 501923 | 2/1999 |
| JP | 2001 514638 | 9/2001 |
| JP | 2002 523507 | 7/2002 |
| JP | 2004 536933 | 12/2004 |
| JP | 2005 531549 | 10/2005 |
| JP | 2006 501272 | 1/2006 |
| JP | 2006 503051 | 1/2006 |
| WO | WO-94 14802 | 7/1994 |
| WO | WO-94 17803 | 8/1994 |
| WO | 95/10506 A1 | 4/1995 |
| WO | WO-96 28429 | 9/1996 |
| WO | WO-97 16456 | 5/1997 |
| WO | WO-97 46569 | 12/1997 |
| WO | WO-98 00434 | 1/1998 |
| WO | 98/10765 A1 | 3/1998 |
| WO | WO-98 16184 | 4/1998 |
| WO | 98/40384 A1 | 9/1998 |
| WO | 99/41253 A1 | 8/1999 |
| WO | 00/18758 A1 | 4/2000 |
| WO | WO-00 43394 | 7/2000 |
| WO | WO-01 05758 | 1/2001 |
| WO | WO-01 60315 | 8/2001 |
| WO | WO-01 77075 | 10/2001 |
| WO | 02/06288 A1 | 1/2002 |
| WO | 02/09713 A2 | 2/2002 |
| WO | WO-02 16348 | 2/2002 |
| WO | 02/055082 A1 | 7/2002 |
| WO | WO-02 057425 | 7/2002 |
| WO | 02/068423 A1 | 9/2002 |
| WO | WO-02 074774 | 9/2002 |
| WO | WO-02 086160 | 10/2002 |
| WO | 02/098864 A1 | 12/2002 |
| WO | WO-03 011925 | 2/2003 |
| WO | WO-03 022859 | 3/2003 |
| WO | 03/037899 A1 | 5/2003 |
| WO | 03/041725 A2 | 5/2003 |
| WO | WO-03 037432 | 5/2003 |
| WO | WO-03 072757 | 9/2003 |
| WO | 03/093269 A2 | 11/2003 |
| WO | WO-03 099840 | 12/2003 |
| WO | WO-2004 002999 | 1/2004 |
| WO | 2004/018474 A1 | 3/2004 |
| WO | 2004/026286 A1 | 4/2004 |
| WO | 2004/026876 A1 | 4/2004 |
| WO | WO-2004 046331 | 6/2004 |
| WO | WO-2004 096811 | 11/2004 |
| WO | WO-2004 099210 | 11/2004 |
| WO | WO-2004 099211 | 11/2004 |
| WO | WO-2004 108139 | 12/2004 |
| WO | WO-2004 113306 | 12/2004 |
| WO | WO-2005 051944 | 6/2005 |
| WO | WO-2005 068436 | 7/2005 |
| WO | WO-2006 076455 | 7/2006 |
| WO | WO-2006 084281 | 8/2006 |
| WO | WO-2006 091905 | 8/2006 |
| WO | WO-2006 125548 | 11/2006 |
| WO | WO-2007 025043 | 3/2007 |
| WO | WO-2007 046747 | 4/2007 |
| WO | WO-2008 005542 | 1/2008 |
| WO | WO-2008 055959 | 5/2008 |
| WO | WO-2008 100447 | 8/2008 |
| WO | WO-2008 104077 | 9/2008 |
| WO | WO-2008 139293 | 11/2008 |
| WO | WO-2009 068617 | 6/2009 |
| WO | WO-2009 121919 | 10/2009 |
| WO | WO-2010 026214 | 3/2010 |
| WO | WO-2010 112437 | 10/2010 |
| WO | WO-2011 018495 | 2/2011 |

OTHER PUBLICATIONS

Freo U, Pizzolato G, Dam M, Ori C, Battistin L.. A short review of cognitive and functional neuroimaging studies of cholinergic drugs: implications for therapeutic potentials. J Neural Transm. May 2002;109(5-6):857-70.*

Related U.S. Appl. No. 13/099,064, filed May 2, 2011.

Related U.S. Appl. No. 12/935,686, filed Sep. 30, 2010.

Related U.S. Appl. No. 13/062,625, filed Mar. 7, 2011.

Related U.S. Appl. No. 12/855,129, filed Aug. 12, 2010.

International Search Report for PCT/EP2010/054050 dated May 27, 2010.

International Preliminary Report on Patentability for PCT/EP2009/061455 dated Mar. 17, 2011.

International Search Report for PCT/EP2009/061455 dated Feb. 19, 2010.

International Preliminary Report on Patentability for PCT/EP2009/053907 dated Oct. 14, 2010.

International Search Report for PCT/EP2008/066350 dated Feb. 23, 2009.

International Search Report for PCT/EP2009/053907 dated May 26, 2009.

Wang, H et al., "Insight into Binding of Phosphodiesterase-9A Selective Inhibitors by Crystal Structures and Mutagenesis," Journal of Medicinal Chemistry, Oct. 12, 2009.

Chem Abstracts Service, Database Chemcats, 2007, Database Accession No. ALB-H01677136, XP 002556399.

Harb et al., Chemical Papers, 2005, vol. 59, No. 3, pp. 187-195, ISSN 0366-6352, XP 002498868.

Hung et al., "A High-Yielding Synthesis of Monoalkylhydrazines", Journal of Organic Chemistry 1981, vol. 46, pp. 5413-5414.

Markwalder, J. et al., "Synthesis and Biological Evaluation of 1-Aryl-4, 5-dihydro-1H-pyrazolo[3,4-d]pyrimidin-4-one Inhibitors of Cyclin-Dependent Kinases", Journal of Med Chemistry, 2004, vol. 47, pp. 5894-5911, XP 002399637.

Medline Article—http://www/nlm.nih.gov/medlineplus/ency/article/000746.htm, Last accessed Jul. 15, 2010.

Prickaerts et al., "Effects of Two Selective Phosphodiesterase Type 5 Inhibitors, Sildenafil and Vardenafil, on Object Recognition Memory and Hippocampal Cyclic GMP Levels in the Rat", Neuroscience, 2002, vol. 113, pp. 351-361.

Schmidt et al.: "Pyrazolo[3,4-d]pyrimidin-nucleoside", Chemische Berichte, 1977, vol. 110, pp. 2445-2455.

Skipper et al., "Structure-Activity Relationships Observed on Screening a Series of Pyrazolopyrimidines against Experimental Neoplasms", Cancer Research, 1957, vol. 17, pp. 579-596.

Timberlake et al., "Chemistry of Hydrazo-,Azo-, and Azoxy Groups", Patai, 1975, Chapter 4.

Ugarkar et al., Journal of Medicinal Chem., 1984, vol. 27, No. 8, pp. 1026-1030.

Van Staveren et al., "Cloning and localization of the cGMP-specific phosphodiesterase type 9 in the rat brain", Journal of Neurocytology, 2002, vol. 31, pp. 729-741.

Wang et al., "Identification and characterization of a new human type 9 cGMP-specific phosphodiesterase splice variant (PDE9A5) Differential tissue distribution and subcellular localization of PDE9A variants", Gene 314 (2003), pp. 15-27.

Accessed on Mar. 18, 2007. http://www.mentalhealth.org.uk/information/mental-health-a-z/dementia/.

Andreeva, Svetlana G., et al; Expression of cGMP-Specific Phosphodiesterase 9A mRNA in the Rat Brain, Journal of Neuroscience (2001) vol. 21, No. 22, pp. 9068-9076.

Bager et al; "Role of Cyclic GMP in the Regulation of Neuronal Calcium and Survival by Secreted Forms of β-Amyloid Precursor," Journal of Neurochemistry (1995) vol. 64, No. 5 pp. 2087-2096.

Bagli, Jehan et al; Chemistry and Positive Inotropic Effect of Pelrinone and related Derivates. A Novel Class of 2-Methylpyrimidones as Inotropic Agents; Journal of Medicinal Chemistry (1988) vol. 31 pp. 814-823.

Byrn, et al; "Solid State Chemistry of Drugs," $2^{nd}$ ed., SSCI, Inc., (1999) Chapter 10 pp. 232-247.

Cheng, C. C. et al; Potential Purine Antagonists VII. Synthesis of 6-Alkylpyrazolo-[3,4-d]pyrimidines; Journal of Organic Chemistry (1958) vol. 23 pp. 191-200.

Database Medline, US national Library of Medicine (NLM), Bethesda, MD, US, 1997. Schousboe, et al., "role of Ca+2 and Other Second Messengers in Excitatory Amino Acid Receptor Mediated Neurodegeneration: Clinical Perspectives," Database Accession No. NLM9186041. Zusammenfassung & Clinical Neuroscience, New York, NY, 1997.

Deninno, Michael P., et al; "The Discovery of Potent, Selective, and Orally Bioavailable PDE9 Inhibitors as Potential Hypoglycemic Agents," Bioorganic & Medicinal chemistry Letters (2009) vol. 19 pp. 2537-2541.

Dorwald, F. Zaragoza; "Side Reactions in Organic Synthesis", A Guide to Successful Systhesis Design, 2005, 4 pages.

Ebert, U., et al; "Scopolamine Model of Dementia: Electroencephalogram Findings and Cognitive Performance"; European Journal of Clinical Investigation (1998) vol. 28, No. 11 pp. 944-949.

Fawcett, Lindsay et al; Molecular Cloning and Characterization of a Distinct Human Phosphodiesterase Gene Family: PDE11A; Proc. Natl. Acad. Sci. (2000) vol. 97, No. 7, pp. 3702-3707.

Fisher, Douglas A. et al; Isolation and Characterization of PDEM, a Novel Human CAMP-Specific Phosphodiesterase; Biochemical and Biophysical Research Communications (1998) vol. 246, pp. 570-577.

Fisher, Douglas A., et al; Isolation and Characterization of PDE8A, A Novel Human cGMP-specific Phosphodiesterase; Journal of Biological Chemistry (1998) vol. 273, No. 25, pp. 15559-15564.

Francis, Sharron H., et al; Characterization of a Novel cGMP Binding Protein from Rat Lung, Journal of Biological Chemistry (1980) vol. 255, No. 2, pp. 620-626.

Fujishige, Kotomi et al; Cloning and Characterization of a Novel Human Phosphodiesterase That Hydrolyzes R21 Both CAMP and cGMP (PDE10A); Journal of Biological Chemistry (1999) vol. 274, No. 26, pp. 18438-.18445.

Gielen, Hieke et al; A Novel Approach to Amidines from Esters; Tetrahedron Letters (2002) vol. 43 pp. 419-421.

Gillespie, Peter G., et al; Characterization of a Bovine Cone Photoreceptor Phosphodiesterase Purified by Cydic GMP-Sepharose Chromatography; Journal of Biological Chemistry (1988) vol. 263. No. 17, pp. 8133-8141.

Gompper, Rudolf et al; Substituted Dithiocarboxylic Acids and Ketene Thioacetals; Institute for Organic Chemistry Technology (1962) vol. 95, pp. 2861-2870. German & English Translation.

Guipponi, Michel et al; Identification and Characterization of a Novel Cydic Nudeotide Phosphodiesterase Gene (PDE8A) That Maps to 21q22.3: Alternative Splicing of mRNA Transcripts, Genomic Structure and Sequence; Hum Genet (1998) vol. 103, pp. 386-392.

Hetman, J. M. et al; Cloning and Characterization of PDE7B, a CAMP-specific Phosphodiesterase, Proc. Natl. Acad. Sci. (2000) vol. 97, No. 1, pp. 472-476.

Huettner, James E. et al; Primary Culture of Identified Neurons from the Visual Cortex of Postnatal Rats; Journal of Neuroscience (1986) vol. 6, pp. 3044-3060.

Internet Article, "Amnesia", From Wikipedia, the free encyclopedia, 3 pages.

International Search Report for corresponding international application PCT/EP03/08880 mailed Apr. 16, 2004.

International Search Report for PCT/EP2004/006477 mailed Oct. 27, 2004.

International Search Report for PCT/03/08923 mailed Dec. 15, 2003.

International Search Report for PCT/EP03/08979 mailed Nov. 25, 2003.

International Search Report for PCT/EP2004/004412 mailed Jul. 14, 2004.

International Search Report for PCT/EP2004/004455 mailed Sep. 17, 2004.

International Search Report for PCT/EP2004/014872 mailed May 19, 2005.

Loughney, Kate et al; Isolation and Characterization of cDNAs Corresponding to Two Human Calcium, Calmodulin-regulated. 3',5'-Cyclic Nucleotide Phosphodiesterases, Journal of Biological Chemistry (1996) vol. 271. No. 2, pp. 796-806.

Loughney, Kate et al; Isolation and Characterization of cDNAs encoding PDE8A, a Human cGMP-Binding, cGMP-Speafic Y.9-Cydic Nudeotide Phosphodiesterase; Gene (1998) vol. 216, pp. 139-147.

Lugnier, Claire; Cyclic Nucleotide Phosphodiesterase (PDE) Superfamily: A New Target for the Development of Specific Therapeutic Agents; Pharmacology & Therapeutics (2006) vol. 109 pp. 366-398.

Martins, Timothy J., et al; Purification and Characterization of a Cydic GMP-stimulated Cyclic Nucledide Phosphodiesterase from Bovine Tissues, Journal of Biological Chemistry (1982) vol. 257, No. 4, pp. 1973-1979.

Miki, Takashi et al; Characterization of the cDNA and Gene Encoding Human PDE3B, the cGIP1 Isoform of the Human Cyclic GMP-Inhibited Cyclic Nucleotide Phosphodiesterase Family; Genomics (1996) vol. 36, pp. 476-485.

Miyashita, Akira et al; Studies on Pyrazolo[3,4-d]Pyrimidine Derivatives. XVIII. Facile Preparation of 1H-Pyrazolo[3,4-d]Pyrimidin-4(5H)-Ones; Heterocycles (1990) vol. 31, No. 7, p. 1309-1314.

Murashima, Seiko et al; Characterization of Particulate Cyclic Nucleotide Phosphodiesterases from Bovine Brain: Purification of a Distinct cGMP-Stimulated Isoenzyme; Biochemistry (1990) vol. 29, No. 22 pp. 5285-5292.

Obernolte, Rena et al; The cDNA of a Human Lymphocyte cyclic-AMP Phosphodiesterase (PDE IV) Reveals a Multigene Family; Gene (1993) vol. 129, pp. 239-247.

Podraza, Kenneth F.; "Reductive Cyclization of Ketoesters Utilizing Sodium Cyanoborohydride: Synthesis of g-and d-Lactones" J. Heterocyclic Chem., 24, 193 (1987).

Prickaerts, J et al; "Possible Role of Nitric Oxide-Cyclic GMP Pathway in ObjectRecognition Memory: Effects of 7-Nitroindazole and Zaprinast," European Journal of Pharmacology (1997) vol. 337, No. 2-3 pp. 125-136.

Reid, I; "Role of Phosphodiesterase Isozymes in the Control of Renin Secretion: Effects of Selective Enzyme Inhibitors," Current Pharmaceutical Design (1999) vol. 5, No. 9 pp. 725-735. (Only Abstract Provided).

Rosman, Guy J., et al; Isolation and Characterization of Human cDNAs encoding a cGMPstimulated 3',5'-Cyclic Nucleotide Phosphodiesterase; Gene (1997) vol. 191, pp. 89-95.

Reddy, K. Hemender et al; Versatile Synthesis of 6-Alkyl/Aryl-1H-Pyrazolo[3,4-d]Pyrimidin-4[5H]-Ones; Indian Journal of Chemistry (1992) vol. 31B, pp. 163-166.

Roenn, Magnus et al; Palladium (II)-Catalyzed Cyclization Using Molecular Oxygen as Reoxidant; Tetrahedron Letters (1995) vol. 36, No. 42, pp. 7749-7752.

Schmidt, P. et al; A New Synthesis of Pyrazolo[3,4-d]Pyrimidines Having Coronary Dilation Properties; Helvetica Chimica Acta (1962) vol. XLV, No. 189, pp. 1620-1627. German & English Translation.

Schousboe, Arne., et al; "Role of Ca++ and Other Second Messengers in Excitatory Amino Acid Receptor Mediated Neurodegeneration: Clinical Perspectives," Clinical Neuroscience (1997) vol. 4 pp. 194-198.

Sonderling, Scott H., et al; Identification and Characterization of a Novel Family of Cyclic Nucleotide Phosphodiesterases; Journal Biology Chemistry (1998) vol. 273, No. 25 pp. 1553-15558.

Sonderling, Scott H., et al; Regulation of CAMP and cGMP signaling: new phosphodiesterases and new functions; Current Opinion in Cell Biology (2000) vol. 12, pp. 174-179.

Ulrich, Joachim; Crystallization: 4. Crystal Characteristics; Kirk-Othmer Encyclopedia of Chemical Technology; Aug. 2002.

Van Der Staay, F. Josef et al; "The novel selective PDE9 inhibitor BAY 73/6691 improves learning and memory in rodents", Neuropharmacology, 55 (2008) pp. 908-916.

Vippagunta, Sudha R. et al; Crystalline Solids; Advanced Drug Delivery Reviews (2001) vol. 48 pp. 3-26.

Weeber E.J., et al; "Molecular Genetics of Human Cognition," Molecular Interventions (2002) vol. 2, No. 6 pp. 376-391.

Wei, Ji-Ye et al; Molecular and Pharmacological Analysis of Cyclic Nucleotide-Gated Channel Function in the Central Nervous System, Progress in Neurobiology (1998) vol. 56, pp. 37-64.

West, Anthony R.; Solid Solutions; John Wiley & Sons, chapter 10 pp. 358 and 365 (1988).

Wunder, Frank, et al;. "Characterization of the First Potent and Selective PDE9 Inhibitor Using a cGMP Reporter Cell Line" Molecular Pharmacology, 68(6) :1775-1781, (2005).

* cited by examiner

SELECTIVE PHOSPHODIESTERASE 9A INHIBITORS AS MEDICAMENTS FOR IMPROVING COGNITIVE PROCESSES

This application is a continuation of U.S. Ser. No. 10/525,119, filed Oct. 14, 2005, now U.S. Pat. No. 7,737,156, issued Jun. 15, 2010; U.S. Ser. No. 10/525,119 is a 371 US National Phase application of PCT/EP2003/008880 filed Aug. 11, 2003.

The invention relates to the use of selective phosphodiesterase 9A (PDE-9A) inhibitors for producing medicaments for improving perception, concentration, learning and/or memory.

The cellular activation of adenylate cyclases and guanylate cyclases effects cyclization respectively of ATP and GTP to 5'-3'cyclic adenosine monophosphate (cAMP) and 5'-3' cyclic guanosine monophosphate (cGMP). These cyclic nucleotides (cAMP and cGMP) are important second messengers and therefore play a central role in cellular signal transduction cascades. Each of them reactivates inter alia, but not exclusively, protein kinases. The protein kinase activated by cAMP is called protein kinase A (PKA), and the protein kinase activated by cGMP is called protein kinase G (PKG). Activated PKA and PKG are able in turn to phosphorylate a number of cellular effector proteins (e.g. ion channels, G-protein-coupled receptors, structural proteins). It is possible in this way for the second messengers cAMP and cGMP to control a wide variety of physiological processes in a wide variety of organs. However, the cyclic nucleotides are also able to act directly on effector molecules. Thus, it is known, for example, that cGMP is able to act directly on ion channels and thus is able to influence the cellular ion concentration (review in: Wei et al., *Prog. Neurobiol.*, 1998, 56: 37-64). The phosphodiesterases (PDE) are a control mechanism for controlling the activity of cAMP and cGMP and thus in turn these physiological processes. PDEs hydrolyze the cyclic monophosphates to the inactive monophosphates AMP and GMP. At least 21 PDE genes have now been described (*Exp. Opin. Investig. Drugs* 2000, 9, 1354-3784). These 21 PDE genes can be divided on the basis of their sequence homology into 11 PDE families (for proposed nomenclature, see http://depts.washington.edu/pde/Nomenclature.html.). Individual PDE genes within a family are differentiated by letters (e.g. PDE1A and PDE1B). If different splice variants within a gene also occur, this is then indicated by an additional numbering after the letters (e.g. PDE1A1).

FIGURES

FIG. 1: Intracellular cGMP concentration in primary rat (E18) cortex cultures after treatment with Example 2. The cells were incubated with Example 2 in the stated concentrations for 20 min The medium control indicates the cGMP level in untreated cells. The DMSO content was 0.2% in the medium controls and in the substance-treated cells. The cGMP concentration is plotted in fmol/150 000 cells.

Figure 2:
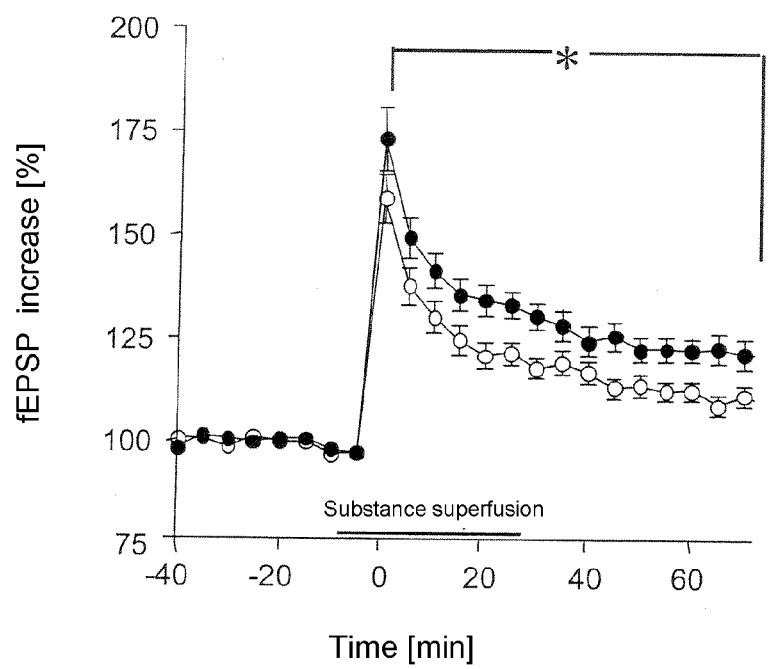

FIG. 2: Effect of Example 2 (10 µM) on the potentiation of the focal excitatory postsynaptic potential (fEPSP) after weak tetanus. Example 2 significantly augmented the increase in the fEPSP when it was flushed in for 10 minutes before to 30 minutes after a weak tetanus (closed symbols). The control was treated with 0.01% DMSO (open symbols). *:p<0.05; analysis of variants with the factors dosage (0 and 10 µM) and test time with the factor measurement time.

Figure 3:
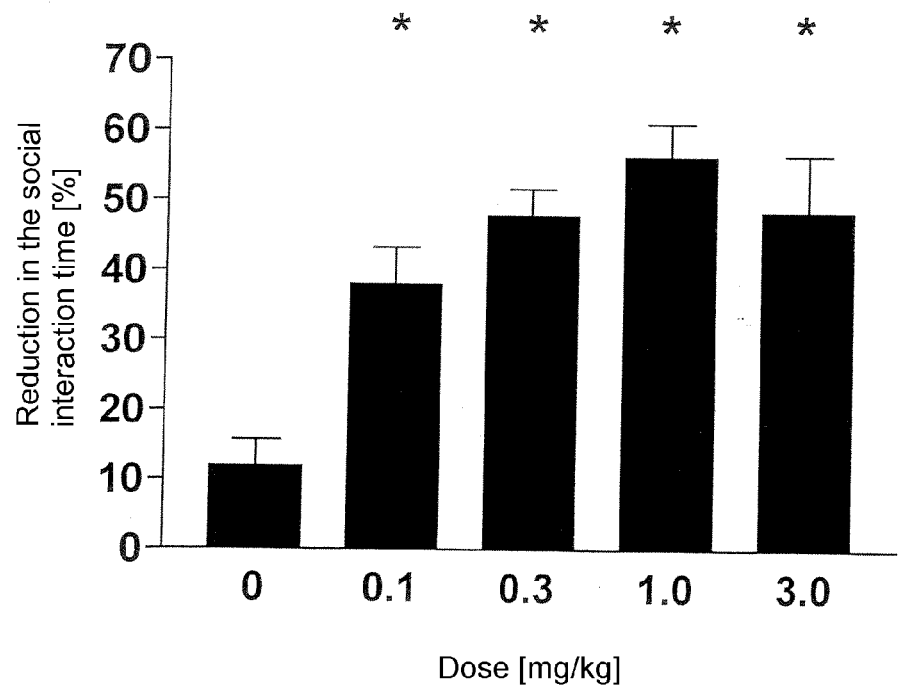

FIG. 3: Effect of Example 2 on the percentage reduction (trial 2/trial 1) in the interaction time in the social recognition test (average+S.E.M.). The animals received intraperitoneal injections of vehicle (10% ethanol, 20% Solutol, 70% physiological saline) or 0.1 mg/kg, 0.3 mg/kg, 1.0 mg/kg or 3.0 mg/kg of Example 2 immediately after the first meeting (trial 1). Statistical analysis: *p<0.05.

PDE9A—DISCOVERY, PROPERTIES, DISTRIBUTION

Human PDE9A (GenBank/EMBL accession number NM_002606, cDNA sequence see Sequence Listing, SEQ ID NO:1) was cloned and sequenced in 1998. The amino acid identity with other PDEs does not exceed 34% (PDE8A) and is never less than 28% (PDE5A). With a Michaelis-Menten constant (Km) of 170 nM, PDE9A has high affinity for cGMP. In addition, PDE9A is selective for cGMP (Km for cAMP=230 µM). PDE9A has no cGMP binding domain (GAF domain) which would suggest allosteric enzyme regulation by cGMP. It was shown in a Western blot analysis that PDE9A is expressed in humans inter alia in testes, brain, small intestine, skeletal muscle, heart, lung, thymus and spleen. The highest expression was found in the brain, small intestine, heart and spleen (Fisher et al., *J. Biol. Chem.*, 1998, 273 (25): 15559-15564). The gene for human PDE9A is located on chromosome 21q22.3 and comprises 21 exons. To date, 20 alternative splice variants of PDE9A have been identified (Guipponi et al., *Hum. Genet.*, 1998, 103: 386-392; Rentero et al., *Biochem. Biophys. Res. Commun.*, 2003, 301: 686-692). Classical PDE inhibitors do not inhibit human PDE9A. Thus, IBMX, dipyridamole, SKF94120, rolipram and vinpocetine show no inhibition on the isolated enzyme in concentrations of up to 100 µM. An $IC_{50}$ of 35 µM has been demonstrated for zaprinast (Fisher et al., *J. Biol. Chem.*, 1998, 273 (25): 15559-15564).

Murine PDE9A was cloned and sequenced in 1998 by Soderling et al. (*J. Biol. Chem.*, 1998, 273 (19): 15553-15558). This has, like the human form, high affinity for cGMP with a Km of 70 nM. Particularly high expression was found in the mouse kidney, brain, lung and heart. Murine PDE9A is not inhibited by IBMX in concentrations below 200 µM either; the $IC_{50}$ for zaprinast is 29 µM (Soderling et al., *J. Biol. Chem.*, 1998, 273 (19): 15553-15558). It has been found that PDE9A is strongly expressed in some regions of the rat brain. These include olfactory bulb, hippocampus, cortex, basal ganglia and basal forebrain (Andreeva et al., *J. Neurosci.*, 2001, 21 (22): 9068-9076). The hippocampus, cortex and basal forebrain in particular play an important role in learning and memory processes.

PDE9A is distinguished by having particularly high affinity for cGMP. The Km for cGMP is 170 µM (Fisher et al., *J. Biol. Chem.*, 1998, 273 (25): 15559-15564). PDE9A is therefore active even at low physiological concentrations, in contrast to PDE2A (Km=10 µM; Martins et al., *J. Biol. Chem.*, 1982, 257: 1973-1979), PDE5A (Km=4 µM; Francis et al., *J. Biol. Chem.*, 1980, 255: 620-626), PDE6A (Km=17 µM; Gillespie and Beavo, *J. Biol. Chem.*, 1988, 263 (17): 8133-8141) and PDE11A (Km=0.52 µM; Fawcett et al., *Proc. Nat. Acad. Sci.*, 2000, 97 (7): 3702-3707). In contrast to PDE2A (Murashima et al., *Biochemistry*, 1990, 29: 5285-5292), the catalytic activity of PDE9A is not increased by cGMP because it has no GAF domain (Beavo et al., *Current Opinion in Cell Biology*, 2000, 12: 174-179). PDE9A inhibitors therefore lead to an increase in the baseline cGMP concentration (see FIG. 1). This increase in the baseline cGMP concentration surprisingly led to an improvement in learning and memory in the social recognition test.

It has surprisingly been demonstrated that PDE9A inhibitors have an effect on the function of the central nervous system. It has now been found in particular that selective PDE9A inhibitors are suitable for producing medicaments for improving perception, concentration, learning or memory.

A PDE9A inhibitor for the purposes of the invention is a compound which inhibits human PDE9A under the conditions indicated below with an $IC_{50}$ of less than 10 μM, preferably less than 1 μM.

A selective PDE9A inhibitor for the purposes of the invention is a compound which inhibits human PDE9A under the conditions indicated below more strongly than human PDE1C, PDE2A, PDE3B, PDE4B, PDE5A, PDE7B, PDE8A, PDE10A and PDE11. $IC_{50}$ (PDE9A)/$IC_{50}$ (PDE1C, PDE2A, PDE3B, PDE4B, PDE5A, PDE7B PDE8A, PDE10A and PDE11A) is preferably less than 0.2.

The selective PDE9A inhibitors are particularly suitable for improving perception, concentration, learning or memory after cognitive impairments like those occurring in particular in situations/diseases/syndromes such as mild cognitive impairment, age-associated learning and memory impairments, age-associated memory losses, vascular dementia, craniocerebral trauma, stroke, dementia occurring after strokes (post stroke dementia), post-traumatic dementia, general concentration impairments, concentration impairments in children with learning and memory problems, Alzheimer's disease, Lewy body dementia, dementia with degeneration of the frontal lobes, including Picks syndrome, Parkinson's disease, progressive nuclear palsy, dementia with corticobasal degeneration, amyotropic lateral sclerosis (ALS), Huntington's disease, multiple sclerosis, thalamic degeneration, Creutzfeld-Jacob dementia, IIIV dementia, schizophrenia with dementia or Korsakoff's psychosis.

The invention relates to the use of selective PDE9A inhibitors for producing medicaments for improving perception, concentration, cognitive processes, learning and/or memory.

The invention further relates to the use of selective PDE9A inhibitors for the prophylaxis and/or treatment of impairments of perception, concentration, cognitive processes, learning and/or memory.

In this connection, the impairment may be inter alia a consequence of a disorder selected from the group of dementia, stroke, craniocerebral trauma, Alzheimer's disease, Parkinson's disease, depression, or dementia with degeneration of the frontal lobes.

The invention further relates to the use of PDE9A inhibitors for the treatment of diseases of the central nervous system which are amenable to therapy through influencing the cGMP levels. Thus, the invention relates for example to the treatment of dementia, stroke, craniocerebral trauma, Alzheimer's disease, dementia with degeneration of the frontal lobes, Lewy body dementia, vascular dementia, attention deficit syndrome, impairments of attention and concentration, Parkinson's disease, schizophrenia, depression, affective disorders, psychoses, neuroses, anxiety, mania or manic depressive disorders, Pick's disease, pain and epilepsy.

The invention preferably relates to the use according to the invention of the PDE9A inhibitors of the formulae

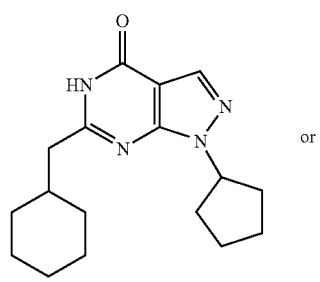

(I)

or

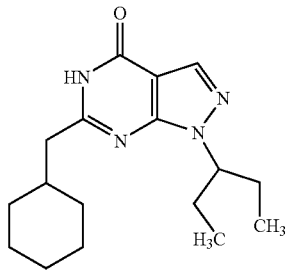

(II)

The compounds of the formulae (I) and (II) may also be in the form of their salts, solvates or solvates of their salts. Physiologically acceptable salts are preferred for the purposes of the invention.

Physiologically acceptable salts may be salts of the compounds of the invention with inorganic or organic acids. Preference is given to salts with inorganic acids such as, for example, hydrochloric acid, hydrobromic acid, phosphoric acid or sulfuric acid, or salts with organic carboxylic or sulfonic acids such as, for example, acetic acid, maleic acid, fumaric acid, malic acid, citric acid, tartaric acid, lactic acid, benzoic acid or methanesulfonic acid, ethanesulfonic acid, benzenesulfonic acid, toluene-sulfonic acid or naphthalene-disulfonic acid.

Physiologically acceptable salts may likewise be metal or ammonium salts of the compounds of the invention. Particular preference is given to alkali metal salts (e.g. sodium or potassium salts), alkaline earth metal salts (e.g. magnesium or calcium salts), and ammonium salts derived from ammonia or organic amines such as, for example, ethylamine, di- or triethylamine, di- or triethanolamine, dicyclohexylamine, dimethylaminoethanol, arginine, lysine, ethylenediamine or 2-phenylethylamine.

WO 98/40384 discloses pyrazolopyrimidines which are excellent PDE1, 2 and 5 inhibitors and can be employed for the treatment of cardiovascular and cerebrovascular disorders and disorders of the urogenital system.

CH 396 924, CH 396 925, CH 396 926, CH 396 927, DE 1 147 234, DE 1 149 013, GB 937,726 describe pyrazolopyrimidines which have a coronary-dilating effect and which can be employed for the treatment of disturbances of myocardial blood flow.

U.S. Pat. No. 3,732,225 describes pyrazolopyrimidines which have an antiinflammatory and blood glucose-lowering effect.

DE 2 408 906 describes styrenepyrazolpyrimidines which can be employed as antimicrobial and antiinflammatory agents for the treatment of, for example, edema.

The compounds of the invention can be prepared by the synthetic scheme described below:

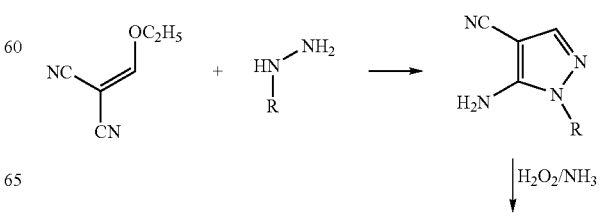

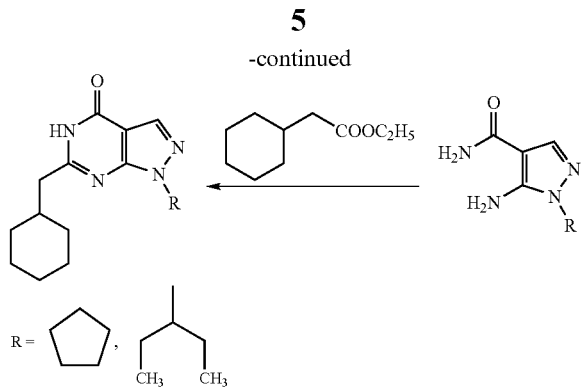

Optional subsequent reaction of the compounds of the formula (I) and (II) with the appropriate (i) solvents and/or (ii) bases or acids leads to the corresponding salts, solvates and/or solvates of the salts.

The active ingredient may have systemic and/or local effects. It can for this purpose be administered in a suitable way, such as, for example, by the oral, parenteral, pulmonary, nasal, sublingual, lingual, buccal, rectal, dermal, transdermal, conjunctival or otic route or as implant.

The active ingredient can be administered in suitable administration forms for these administration routes.

Administration forms suitable for oral administration are those which function according to the state of the art and deliver the active ingredient in a rapid and/or modified way, such as, for example, tablets (uncoated or coated tablets, for example with coatings which are resistant to gastric juice), capsules, sugar-coated tablets, granules, pellets, powders, emulsions, suspensions or solutions.

Parenteral administration can take place with avoidance of an absorption step (intravenous, intraarterial, intracardiac, intraspinal or intralumbar) or with inclusion of an absorption (intramuscular, subcutaneous, intracutaneous, percutaneous or intraperitoneal). Administration forms suitable for parenteral administration are, inter alia, injection and infusion preparations in the form of solutions, suspensions, emulsions, lyophilizates or sterile powders.

Examples suitable for other administration routes are medicinal forms for inhalation (inter alia powder inhalators, nebulizers), nasal drops/solutions, sprays; tablets or capsules for lingual, sublingual or buccal administration, suppositories, preparations for the ears or eyes, vaginal capsules, aqueous suspensions (lotions, shaking mixtures), lipophilic suspensions, ointments, creams, milk, pastes, foams, dusting powders or implants.

The active ingredients can be converted in a manner known per se into the stated administration forms. This takes place by using inert, non-toxic, pharmaceutically suitable excipients. These include, inter alia, carriers (for example microcrystalline cellulose), solvents (e.g. liquid polyethylene glycols), emulsifiers (for example sodium dodecyl sulfate), dispersants (for example polyvinylpyrrolidone), synthetic and natural biopolymers (for example albumin), stabilizers (e.g. antioxidants such as ascorbic acid), colors (e.g. inorganic pigments such as iron oxides) and masking tastes and/or odors.

It has generally proved advantageous on parenteral administration to administer amounts of about 0.001 to 30 mg/kg, preferably about 0.01 to 10 mg/kg of body weight to achieve effective results. The amount on oral administration is about 0.01 to 100 mg/kg, preferably about 0.1 to 30 mg/kg of body weight.

It may nevertheless be necessary to deviate from the stated amounts, in particular as a function of body weight, administration route, individual behavior toward the active ingredient, type of preparation and time or interval over which administration takes place.

PDE Inhibition

Recombinant PDE1C (GenBank/EMBL Accession Number: NM_005020, Loughney et al. *J. Biol. Chem.* 1996 271, 796-806), PDE2A (GenBank/EMBL Accession Number: NM_002599, Rosman et al. *Gene* 1997 191, 89-95), PDE3B (GenBank/EMBL Accession Number: NM_000922, Miki et al. *Genomics* 1996, 36, 476-485), PDE4B (GenBank/EMBL Accession Number: NM_002600, Obernolte et al. *Gene.* 1993, 129, 239-247), PDE5A (GenBank/EMBL Accession Number: NM_001083, Loughney et al. *Gene* 1998, 216, 139-147), PDE7B (GenBank/EMBL Accession Number: NM_018945, Hetman et al. *Proc. Natl. Acad. Sci. U.S.A.* 2000, 97, 472-476), PDE8A (GenBank/EMBL Accession Number: AF_056490, Fisher et al. *Biochem. Biophys. Res. Commun.* 1998 246, 570-577), PDE9A (GenBank/EMBL accession number NM_002606, cDNA sequence see Sequence Listing, SEQ ID No: 1, Fisher et al., *J. Biol. Chem,* 1998, 273 (25): 15559-15564), PDE10A (GenBank/EMBL Accession Number: NM_06661, Fujishige et al. *J. Biol. Chem.* 1999, 274, 18438-45), PDE11A (GenBank/EMBL Accession Number: NM_016953, Fawcett et al. *Proc. Natl. Acad. Sci.* 2000, 97, 3702-3707) were expressed in Sf9 cells with the aid of the pFASTBAC baculovirus expression system (GibcoBRL). 48 h after the infection, the cells are harvested and suspended in 20 mL (per 1 L of culture) of lysis buffer (50 mM tris-HCl, pH 7.4, 50 mM NaCl, mM MgCl$_2$, 1.5 mM EDTA, 10% glycerol plus 20 µL of protease inhibitor cocktail set III [CalBiochem, La Jolla, Calif. USA]). The cells are treated with ultrasound at 4° C. for 1 minute and subsequently centrifuged at 10000 rpm and 4° C. for 30 minutes. The supernatant (PDE preparation) was collected and stored at −20° C.

The test substances are dissolved in 100% DMSO and serially diluted to determine their in vitro effect on PDE 9A. Typically, serial dilutions from 200 µM to 1.6 µM are prepared (resulting final concentrations in the assay: 4 µM to 0.032 µM). 2 µL portions of the diluted substance solutions are introduced into the wells of microtiter plates (Isoplate; Wallac Inc., Atlanta, Ga.). Then 50 µL of a dilution of the PDE9A preparation described above are added. The dilution of the PDE9A preparation is chosen so that less than 70% of the substrate is converted during the subsequent incubation (typical dilution: 1:10000; dilution buffer: 50 mM Tris/HCl pH 7.5, 8.3 mM MgCl$_2$, 1.7 mM EDTA, 0.2% BSA). The substrate, [8-$^3$H] guanosine 3',5'-cyclic phosphate (1 µCi/µL; Amersham Pharmacia Biotech., Piscataway, N.J.) is diluted 1:2000 with assay buffer (50 mM Tris/HCl pH 7.5, 8.3 mM MgCl$_2$, 1.7 mM EDTA) to a concentration of 0.0005 µCi/µL. The enzyme reaction is finally started by adding 50 µL (0.025 µCi) of the diluted substrate. The assay mixtures are incubated at room temperature for 60 min and the reaction is stopped by adding 25 µl of a PDE9A inhibitor (e.g. the inhibitor from preparation example 1, final concentration 10 µM) dissolved in assay buffer. Immediately thereafter, 25 µL of a suspension containing 18 mg/mL Yttrium Scintillation Proximity Beads (Amersham Pharmacia Biotech., Piscataway, N.J.) are added. The microtiter plates are sealed with a film and left to stand at room temperature for 60 min. The plates are then measured for 30 s per well in a Microbeta scintillation counter (Wallac Inc., Atlanta, Ga.). IC$_{50}$ values are determined from the graphical plot of the substance concentration versus the percentage inhibition.

The in vitro effect of test substances on recombinant PDE3B, PDE4B, PDE7B, PDE8A, PDE10A and PDE11A is determined in accordance with the assay protocol described above for PDE 9A with the following adaptations: [5',8-$^3$H] adenosine 3',5'-cyclic phosphate (1 µCi/µL; Amersham Pharmacia Biotech., Piscataway, N.J.) is used as substrate. Addition of an inhibitor solution to stop the reaction is unnecessary. Instead, the incubation of substrate and PDE is followed immediately by addition of the yttrium scintillation proximity beads as described above and thus the reaction is stopped. To determine a corresponding effect on recombinant PDE1C, PDE2A and PDE5A, the protocol is additionally adapted as follows: with PDE1C, additionally $10^{-7}$ M calmodulin and 3 mM $CaCl_2$ are added to the reaction mixture. PDE2A is stimulated in the assay by adding 1 µM cGMP and is assayed with a BSA concentration of 0.01%. The substrate employed for PDE1C and PDE2A is [5',8-$^3$H] adenosine 3',5'-cyclic phosphate (1 µCi/µL; Amersham Pharmacia Biotech., Piscataway, N.J.), and for PDE5A is [8-$^3$H] guanosine 3',5'-cyclic phosphate (1 µCi/µL; Amersham Pharmacia Biotech., Piscataway, N.J.).

Inhibition of PDE isoenzymes by Example 2

| Isoenzyme | Species | IC$_{50}$ [nM] |
|---|---|---|
| PDE1C | human | 720 |
| PDE2A | human | >4000 |
| PDE3B | human | >4000 |
| PDE4B | human | >4000 |
| PDE5A | human | >4000 |
| PDE7B | human | >4000 |
| PDE8A | human | >4000 |
| PDE9A | human | 110 |
| PDE10A | human | >4000 |
| PDE11 | human | >4000 |

The PDE9A-inhibiting effect of Example 1 can be verified experimentally by an IC$_{50}$ of IC$_{50}$=5 nM.

Increasing the Intracellular Neuronal cGMP Concentration in Cell Cultures

PDE9A inhibitors increase the intracellular neuronal cGMP in cultivated primary cortical neurons.

Rat embryos (embryonic day E17-E19) were decapitated, and the heads were transferred into dissection dishes filled with dissection medium (DMEM, penicillin/streptomycin; both from Gibco). The scalp and the roof of the skull were removed, and the exposed brains were transferred into another Petri dish with dissection medium. Using a binocular microscope and two forceps, the cerebrum (cortex) was isolated and cooled to 4° C. with ice. This dissection and the isolation of the cortical neurons were then carried out in accordance with a standard protocol using the Papain kit (Worthington Biochemical Corporation, Lakewood, N.J. 08701, USA) (Huettner et al. *J. Neurosci.* 1986, 6, 3044-3060). The mechanically isolated cortical neurons were cultivated at 150,000 cells/well in 200 µl of neurobasal medium/well (neurobasal; B27 supplement; 2 mM L-glutamine; in the presence of penicillin/streptomycin; all agents from Gibco) in 96-well plates (pretreated with poly-D-lysine/100 µg/ml for 30 min.) under standard conditions (37° C., 5% $CO_2$) for 7 days. After 7 days, the medium was removed and the cells were washed with HBSS buffer (Hank's balanced salt solution, Gibco/BRL). Subsequently, 100 µl of test substance of Example 2 dissolved in HBSS buffer (previously dissolved in 100% DMSO: 10 mM) were put on the cells. Subsequently, a further 100 µl of HBSS buffer were added, so that the final concentration of the test substance of Example 2 was as indicated in FIG. 1, and incubated at 37° C. for 20 min. The assay buffer was then completely removed. Subsequently, the cells were lyzed in 200 µl of lysis buffer (cGMP kit code RPN 226; from Amersham Pharmacia Biotech.), and the cGMP concentration was measured as stated by the manufacturer. All measurements were carried out in triplicate. Statistical analysis took place using Prism Software Version 2.0 (GraphPad Software Inc., San Diego, Calif. USA).

Incubation of the primary neurons with Example 2 led to an increase in the cGMP content (FIG. 1).

Long-Term Potentiation

Long-term potentiation is regarded as a cellular correlate of learning and memory processes. The following method was used to determine whether PDE 9 inhibition has an influence on long-term potentiation:

Rat hippocampi were placed at an angle of about 70 degrees to the cutting blade (chopper). 400 µm-thick slices of the hippocampus were prepared. The slices were removed from the blade using a very soft, thoroughly wetted brush (marten hair) and transferred into a glass vessel with cold nutrient solution (124 mM NaCl, 4.9 mM KCl, 1.3 mM $MgSO_4 \times 7$ $H_2O$, 2.5 mM $CaCl^{2+}$ anhydrous, 1.2 mM $KH_2PO_4$, 25.6 mM $NaHCO_3$, 10 mM glucose, pH 7.4) gassed with 95% $O_2$/5% $CO_2$. During the measurement, the slices were kept in a temperature-controlled chamber under a 1-3 mm-high liquid level. The flow rate was 2.5 ml/min The preliminary gassing took place under a slightly elevated pressure (about 1 atm) and through a microneedle in the prechamber. The slice chamber was connected to the prechamber in such a way that a minicirculation could be maintained. The minicirculation is driven by the 95% $O_2$/5% $CO_2$ flowing out through the microneedle. The freshly prepared hippocampus slices were adapted in the slice chamber at 33° C. for at least 1 hour.

The stimulus level was chosen so that the focal excitatory postsynaptic potentials (fEPSP) were 30% of the maximum excitatory postsynaptic potential (EPSP). A monopolar stimulation electrode consisting of lacquered stainless steel, and a constant-current biphasic stimulus generator (AM Systems 2100) were used for local stimulation of the Schaffer collaterals (voltage: 1-5 V, pulse width of one polarity 0.1 ms, total pulse 0.2 ms). Glass electrodes (borosilicate glass with filament, 1-5 MOhm, diameter: 1.5 mm, tip diameter: 3-20 µm), filled with normal nutrient solution, were used to record the excitatory postsynaptic potentials (fEPSP) from the stratum radiatum. The field potentials were measured versus a chlorinated silver reference electrode located at the edge of the slice chamber using a DC voltage amplifier. The field potentials were filtered through a low-pass filter (5 kHz). The slope of the fEPSPs (fEPSP slope) was determined for the statistical analysis of the experiments. The recording, analysis and control of the experiment took place with the aid of a software program (PWIN) which was developed in the Department of Neurophysiology of the Leibniz Neurobiology Institute, Magdeburg. The formation of the average fEPSP slopes at the respective time points and construction of the diagrams took place with the aid of the EXCEL software, with automatic data recording by an appropriate macro.

In the control experiments, the baseline synaptically transmission was initially recorded for 60-120 minutes. Subsequently, two double pulses were administered four times at an interval of 200 ms, with an interpulse interval of 10 ms for the double pulses and a width of 0.2 ms for the individual pulses (weak tetanus) (time=0 minutes in FIG. 2). The resulting potentiation of the EPSPs was recorded for at least 60 minutes. Example 2 was flushed in for 10 minutes before up to 30 minutes after the stimulation in the experiment depicted.

Superfusion of the hippocampus slices with a 10 µM solution of Example 2 led to a significant increase in the LTP (FIG. 2).

Social Recognition Test:

The social recognition test is a learning and memory test. It measures the ability of rats to distinguish between known and unknown members of the same species. This test is therefore suitable for examining the learning- or memory-improving effect of test substances.

Adult rats housed in groups were placed singly in test cages 30 min before the start of the test. Four minutes before the start of the test, the test animal was put in an observation box. After this adaptation time, a juvenile animal was put in with the test animal and the absolute time for which the adult animal inspected the young one was measured for 2 min (trial 1). All behaviors clearly directed at the young animal were measured, i.e. anogenital inspection, pursuit and grooming, during which the old animal was no further than 1 cm from the young animal. The juvenile was then removed, and the adult was treated with Example 2 or vehicle and subsequently returned to its own cage. The test was repeated after a retention time of 24 hours (trial 2). A diminished social interaction time compared with trial 1 would indicate that the adult rat remembers the young animal.

The adult animals received intraperitoneal injections directly following trial 1 either with vehicle (10% ethanol, 20% Solutol, 70% physiological saline) or 0.1 mg/kg, 0.3 mg/kg, 1.0 mg/kg or 3.0 mg/kg of Example 2 dissolved in 10% ethanol, 20% Solutol, 70% physiological saline. Vehicle-treated rats showed no reduction in the social interaction time in trial 2 compared with trial 1. They had consequently forgotten that they had already had contact with the young animal. Surprisingly, the social interaction time in the second run after treatment Example 2 was significantly reduced compared with those treated with vehicle. This means that the substance-treated rats have remembered the juvenile animal and thus Example 2 displayed an improving effect on learning and memory.

Abbreviations Used

| | |
|---|---|
| DMSO | dimethyl sulfoxide |
| equiv. | equivalent(s) |
| ESI | electrospray ionization (in MS) |
| HPLC | high pressure, high performance liquid chromatography |
| MS | mass spectroscopy |
| m.p. | melting point |
| NMR | nuclear magnetic resonance spectroscopy |

EXEMPLARY EMBODIMENTS

Example 1

6-(Cyclohexylmethyl)-1-cyclopentyl-1,5-dihydro-4H-pyrazolo[3,4-d]pyrimidin-4-one

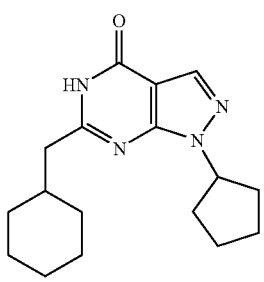 [SMILES: O=c1[nH]c(CC2CCCCC2)nc2c1cnn2C1CCCC1]

Stage 1a)

5-Amino-1-cyclopentyl-1H-pyrazole-4-carbonitrilie

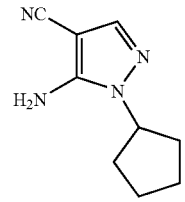

Cyclopentylhydrazine (6.5 g, 64.9 mmol) is slowly added to a solution of ethoxymethylenemalononitrile (7.93 g, 64.9 mmol) in 100 ml of methanol at room temperature under argon, subsequently heated under reflux for 3 h and then stirred at room temperature overnight. The solvent is stripped off in a rotary evaporator and the residue is stirred with diethyl ether. The solid is filtered off with suction, washed with diethyl ether and dried under high vacuum.

Yield: 7.24 g (63% of theory)

MS (ESI): m/z=177 (M+H)$^+$ $^1$H-NMR (200 MHz CDCl$_3$): δ=7.5 (s, 1H), 4.45 (br. s, 2H), 4.35 (m, 1H), 2.2-1.55 (m, 6H) ppm.

Stage 1b)

5-Amino-1-cyclopentyl-1H-pyrazole-4-carboxamide

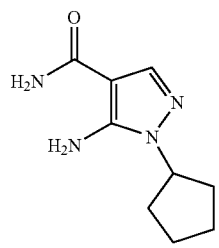 [SMILES: NC(=O)c1cnn(C2CCCC2)c1N]

85 ml of 30% strength hydrogen peroxide solution are added to a solution of 5-amino-1-cyclopentyl-1H-pyrazole-4-carbonitrile (6.74 g, 38.3 mmol) in a mixture of 300 ml of ethanol and 371 ml of concentrated aqueous ammonia solution at room temperature and stirred at room temperature overnight. The nonaqueous solvents are then stripped off in a rotary evaporator. The product precipitates as solid from the remaining mixture and is filtered off with suction, washed with diethyl ether and dried under high vacuum.

Yield: 5.31 g (71% of theory)

MS(ESI): m/z=195 (M+H)$^+$ $^1$H-NMR (200 MHz, CdCl$_3$): δ=7.5 (s, 1H), 5.67-4.8 (broad, 4H), 4.35 (m, 1H), 2.2-1.55 (m, 8H) ppm.

Stage 1c)

6-(Cyclohexylmethyl)-1-cyclopentyl-1,5-dihydro-4H-pyrazolo[3,4-d]pyrimidin-4-one

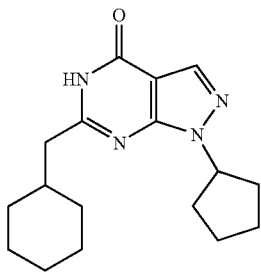 [SMILES: O=c1[nH]c(CC2CCCCC2)nc2c1cnn2C1CCCC1]

Under argon, 75 mg (0.39 mmol) of 5-amino-1-cyclopentyl-1H-pyrazole-4-carbox-amide and 183 mg (1.16 mmol, 3 equiv.) of methyl cyclohexylacetate are introduced into 1.5 ml of absolute ethanol. At 0° C., 54 mg of sodium hydride (60% dispersion in mineral oil; 1.35 mmol, 3.5 equiv.) are slowly added in a countercurrent of argon. The resulting mixture is slowly heated and stirred under reflux for 18 h. For workup, 20 ml of water are added, and the mixture is extracted several times with ethyl acetate. The combined organic phases are dried over sodium sulfate and concentrated in vacuo. The crude product is purified by preparative HPLC.

Yield: 36 mg (31% of theory)

MS (ESI): m/z=301 (M+H)$^+$ m.p.: 147° C.

$^1$H-NMR (300 MHz, DMSO-d$_6$): δ=11.95 (s, 1H), 8.0 (s, 1H), 5.1 (m, 1H), 2.5 (d, 2H), 2.15-1.75 (m, 7H), 1.75-1.55 (m, 7H), 1.3-0.9 (m, 5H) ppm.

Example 2

6-(Cyclohexylmethyl)-1-(1-ethylpropyl)-1,5-dihydro-4H-pyrazolo[3,4-d]-pyrimidin-4-one

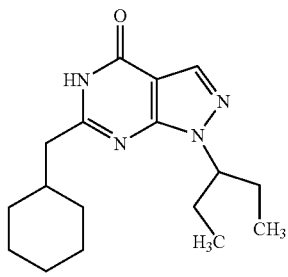 [SMILES: CCC(CC)n1ncc2c(=O)[nH]c(CC3CCCCC3)nc21]

Stage 2a)

5-Amino-1-(1-ethylpropyl)-1H-pyrazole-4-carbonitrile

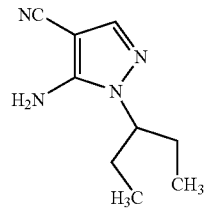

Preparation takes place in analogy to the method for Example 1/stage 1a).

MS (ESI): m/z=179 (M+H)$^+$ $^1$H-NMR (300 MHz, DMSO-d$_6$): δ=7.55 (s, 1H), 6.45 (s, 2H), 4.0 (m, 1H), 1.8-1.55 (m, 4H), 0.65 (t, 6H) ppm.

Stage 2b)

5-Amino-1-(1-ethylpropyl)-1H-pyrazole-4-carboxamide

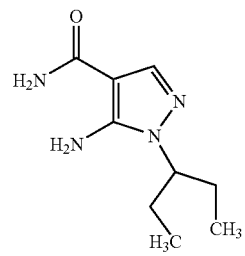

Preparation takes place in analogy to the method for Example 1/stage 1b).

MS (ESI): m/z=197 (M+H)$^+$ $^1$H-NMR (300 MHz, DMSO-d$_6$): δ=7.65 (s, 1H), 6.9 (br. s, 2H), 6.1 (s, 2H), 3.9 (m, 1H), 1.85-1.6 (m, 4H), 0.7 (t, 6H) ppm.

Stage 2c)

6-(Cyclohexylmethyl)-1-(1-ethylpropyl)-1,5-dihydro-4H-pyrazolo[3,4-d]pyrimidin-4-one

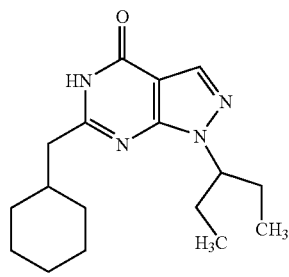

The product is obtained in analogy to Example 1/stage 1c) starting from 200 mg (1.02 mmol) of 5-amino-1-(1-ethylpropyl)-1H-pyrazole-4-carboxamide and 482 mg (3.06 mmol) of methyl cyclohexylacetate.

Yield: 146 mg (47% of theory)
MS (ESI): m/z=303 (M+H)$^+$
m.p.: 122° C.
$^1$H-NMR (200 MHz, DMSO-d$_6$): δ=12.0 (s, 1H), 8.0 (s, 1H), 4.45 (m, 1H), 2.5 (m, 2H), 2.0-1.5 (m, 10H), 1.4-0.9 (m, 5H), 0.6 (t, 6H, J=7.5 Hz) ppm.

The invention claimed is:

1. A method for treating an impairment of perception, concentration, cognitive processes, learning and/or memory, which impairment is a consequence of dementia, stroke, craniocerebral trauma, dementia with degeneration of the frontal lobes, Lewy body dementia, vascular dementia, attention deficit syndrome, Parkinson's disease, schizophrenia, depression, affective disorders, psychoses, neuroses, anxiety, mania, a manic depressive disorder, Pick's disease, pain or epilepsy which comprises administering to a patient an effective amount of a selective PDE9A inhibitor compound,
  wherein the selective PDE9A inhibitor inhibits human PDE9A with an IC$_{50}$ of less than 10 μM, and
  wherein the selective PDE9A inhibitor inhibits human PDE9A more strongly than it inhibits human PDE1C, PDE2A, PDE3B, PDE4B, PDE5A, PDE7B, PDE8A, PDE10A and PDE11.

2. The method of claim 1, where the impairment is a consequence of stroke, craniocerebral trauma, Parkinson's disease, depression, or dementia with degeneration of the frontal lobes.

3. The method of claim 1, where the selective PDE9A inhibitor is a compound of the formula (I) or (II):

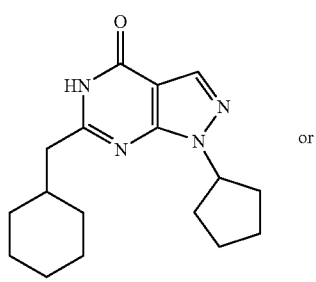

(I)

or

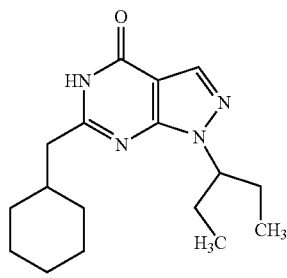 [SMILES: CCC(CC)n1ncc2c(=O)[nH]c(CC3CCCCC3)nc21]

(II)

or a salt, solvate or solvate of a salt thereof.

4. The method of claim 1, wherein the selective PDE9A inhibitor inhibits huma PDE9A with an IC$_{50}$ of less than 1 μM.

5. The method of claim 1, wherein the ratio of the IC$_{50}$ of the selective PDE9A inhibitor to PDE9A to the IC$_{50}$ of the selective PDE9A inhibitor to each of PDE1C, PDE2A, PDE3B, PDE4B, PDE5A, PDE7B PDE8A, PDE10A and PDE11A, is less than 0.2.

6. The method of claim 1, wherein the selective PDE9A inhibitor is administered parenterally in an amount of about 0.001 to 30 mg/kg of body weight.

7. The method of claim 1, wherein the selective PDE9A inhibitor is administered parenterally in an amount of about 0.01 to 10 mg/kg of body weight.

8. The method of claim 1, wherein the selective PDE9A inhibitor is administered orally in an amount of about 0.01 to 100 mg/kg of body weight.

9. The method of claim 1, wherein the selective PDE9A inhibitor is administered orally in an amount of about 0.1 to 30 mg/kg of body weight.

* * * * *